(12) United States Patent
Brevnov

(10) Patent No.: US 6,942,974 B2
(45) Date of Patent: Sep. 13, 2005

(54) SELECTIVE ELUTION OF IMMOBILIZED MULTIPLEXED PRIMER EXTENSION PRODUCTS

(75) Inventor: Maxim G. Brevnov, San Diego, CA (US)

(73) Assignee: Applera Corporation, Foster City, CA (US)

(*) Notice: Subject to any disclaimer, the term of this patent is extended or adjusted under 35 U.S.C. 154(b) by 0 days.

(21) Appl. No.: 10/096,176

(22) Filed: Mar. 8, 2002

(65) Prior Publication Data

US 2003/0194706 A1 Oct. 16, 2003

(51) Int. Cl.[7] .......................... C07H 21/04; C12Q 1/68
(52) U.S. Cl. .................. 435/6; 435/91.1; 435/91.2; 435/287.2; 536/23.1; 536/24.3
(58) Field of Search .................. 435/6, 91.1, 91.2, 435/287.2; 536/23.1, 24.3

(56) References Cited

U.S. PATENT DOCUMENTS 6,124,092 A * 9/2000 O'Neill et al. ................ 435/6
2003/0148277 A1 * 8/2003 Chiesa et al. ................. 435/6

FOREIGN PATENT DOCUMENTS

WO WO 02/10182 * 2/2002 ........... C07H/21/00

* cited by examiner

*Primary Examiner*—Jeanine A. Goldberg
(74) *Attorney, Agent, or Firm*—Jones Day

(57) ABSTRACT

The present invention provides methods and kits for the sequential elution of families of extension products from one or more substrates. The methods and kits can be used, for example, to separate families of primer extension products generated by multiplex sequencing reactions or by other multiplex primer extension reactions.

13 Claims, 5 Drawing Sheets

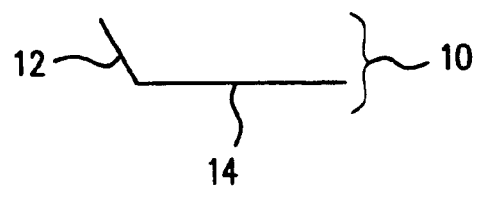
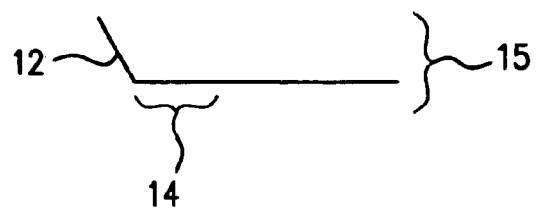
FIG.1
FIG.2
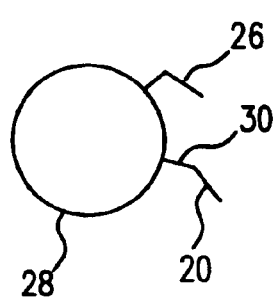
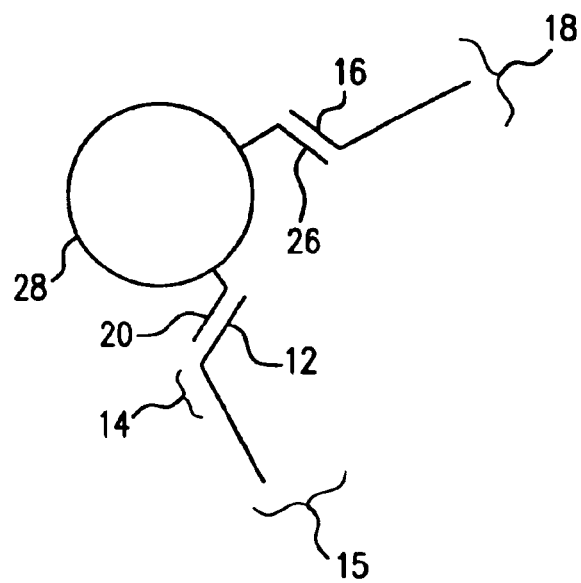
FIG.3
FIG.4

SELECTIVE ELUTION OF IMMOBILIZED MULTIPLEXED PRIMER EXTENSION PRODUCTS

1. FIELD OF THE INVENTION

The present invention relates to multiplex capture and recovery of polynucleotides.

2. BACKGROUND OF THE INVENTION

Many techniques in molecular biology depend upon the generation of polynucleotides by primer extension reactions. The efficiency of such techniques can be increased by multiplexing primer extension reactions. However, improved methods of separating multiplexed families of primer extension products are needed to further enhance the efficiency of such techniques.

3. SUMMARY OF THE INVENTION

In one aspect, the present invention provides methods and kits for the sequential elution of families of extension products from one or more substrates. The methods and kits can be used, for example, to separate families of primer extension products generated by multiplex sequencing reactions or by other multiplex primer extension reactions. Generally, the methods and kits are used to elute selectively families of primer extension products captured on a capture substrate. According to the method, a first captured family of extension products is selectively eluted from the capture substrate. Elution can be accomplished by contacting the captured family of primer extension products with a first specific elution compound that is capable of selectively eluting the first captured family of primer extension products. Remarkably, a second captured family of primer extension products can then be contacted with a second specific elution compound to elute the second captured family of primer extension products. The method can be extended to elute sequentially any number of captured families of primer extension products.

A family of primer extension products comprises polynucleotides that can be captured on a capture substrate, discussed below, and selectively eluted therefrom with the a specific elution compound. A family of primer extension products can be, for instance, a sequencing ladder of polynucleotides or a mixture of amplification products. Typically, each member of a family of primer extension products bears a prey moiety that can be selectively immobilized on a capture substrate. Prey moieties can belong to any class of molecule such as polynucleotides, carbohydrates, polypeptides and other classes of molecules known to those of skill in the art to be capable of specific binding. Examples of suitable prey moieties include members of specific binding pairs of molecules known to those of skill in the art such as biotin, avidin, antibodies, antigens, ligands, receptors and polynucleotides. Examples of prey moieties also include polynucleotides capable of hybridizing with polynucleotide capture compounds, discussed below.

A family of primer extension products comprising a prey moiety can be prepared according to methods well known to those of skill in the art. Typically, a family of primer extension products can be generated by a primer extension reaction from a capturable primer. A capturable primer is a polynucleotide comprising a priming moiety and a prey moiety. The priming moiety is capable of priming a polynucleotide extension reaction.

A family of primer extension products can be captured by any method known to those of skill in the art. For instance, if each member of a family of primer extension products comprises a prey moiety, the family can be captured with a capture substrate corresponding to the prey moiety. A capture substrate corresponds to a prey moiety if the capture substrate comprises a capture compound that is capable of selectively binding the prey moiety as discussed below.

As used in the methods of the invention, a capture substrate is one or more solid supports having capture compounds immobilized thereon that can be used to reversibly capture one or more families of primer extension products. Capture compounds can be bound to the capture substrate by any means known to one of skill in the art for immobilizing molecules. A capture substrate can comprise multiple solid supports, each having immobilized thereon one or more capture compounds. Alternatively, a capture substrate can comprise a single support having immobilized thereon one or more capture compounds.

A capture compound is a compound capable of selectively binding one or more prey moieties in a mixture of families of primer extension products. For instance, if a prey moiety is a polynucleotide, then a corresponding capture compound can be a polynucleotide that is capable of hybridizing to the prey moiety. Like prey moieties, capture compounds can belong to any class of molecule such as polynucleotides, carbohydrates, polypeptides and other classes of molecules known to those of skill in the art to be capable of selective binding. Examples of suitable capture compounds include members of specific binding pairs of molecules known to those of skill in the art such as biotin, avidin, antibodies, antigens, ligands, receptors and polynucleotides. Examples of suitable capture compounds also include polynucleotides that selectively hybridize to polynucleotide prey moieties.

According to the methods of the present invention, individual captured families of primer extension products may be selectively eluted from a capture substrate sequentially by contacting the captured family with specific elution compounds. A specific elution compound is a compound that selectively binds a capture compound or a prey moiety and/or is able to selectively disrupt the interaction between a capture compound and a prey moiety. A specific elution compound is used, for instance, to competitively elute a captured family of primer extension products. Specific elution compounds can belong to any class of compounds such as polynucleotides, carbohydrates, polypeptides and other classes of molecules known to those of skill in the art to be capable of specific binding. Examples of specific elution compounds include polynucleotides that selectively hybridize to polynucleotide capture compounds or to polynucleotide prey moieties thereby selectively disrupting the binding interaction between the polynucleotide capture compounds and their corresponding polynucleotide prey moieties.

According to an embodiment of the method of the present invention, contacting a plurality of captured families of primer extension products with a first specific elution compound can elute a first family of primer extension products. After optional washing, contacting the mixture of captured families of primer extension products with a second specific elution compound can elute a second family of primer extension products. Any number of captured families of primer extension products can be selectively and sequentially eluted in this manner. Pluralities of captured families may be simultaneously selectively eluted by contacting the captured families with a plurality of specific elution compounds.

In another aspect, the present invention provides kits for the isolation of captured families of polynucleotide primer extension products. The kits comprise a plurality of capturable primers, a capture substrate corresponding to the capturable primers and a plurality of specific elution compounds each of that is capable of selectively eluting a family of primer extension products from the capture substrate.

The methods can be applied to any application wherein specific elution of captured primer extension products is desirable. For example, the present invention is useful for the separation of the products of high-throughput multiplexed primer extension of polynucleotides.

4. BRIEF DESCRIPTION OF THE FIGURES

FIG. 1 illustrates a capturable primer;

FIG. 2 illustrates a primer extension product generated from a capturable primer;

FIG. 3 illustrates a capture substrate comprising capture compounds;

FIG. 4 illustrates captured primer extension products;

Figure 5:
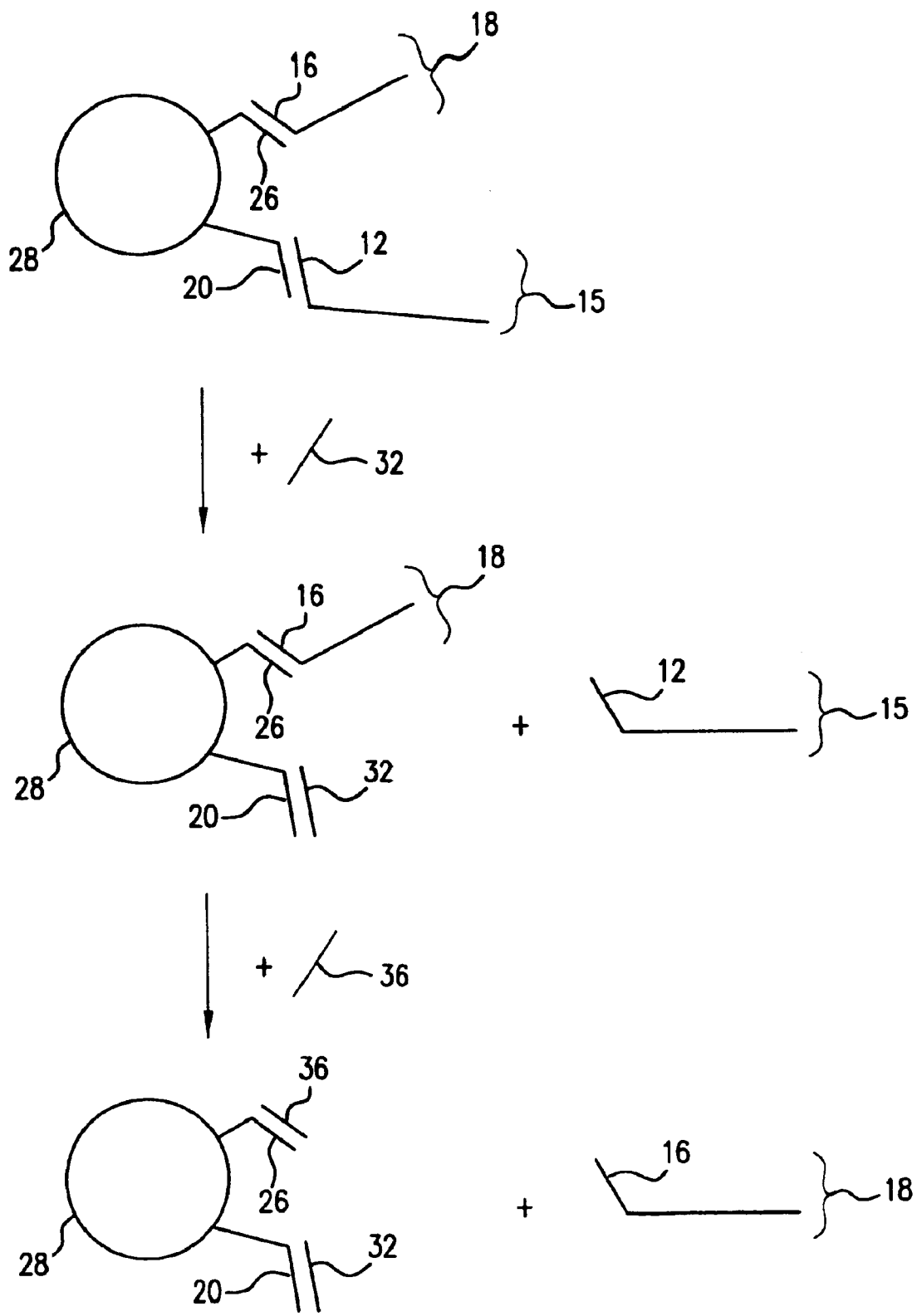
FIG. 5 illustrates selective elution of captured primer extension products from a capture substrate.

5. DETAILED DESCRIPTION OF THE PREFERRED EMBODIMENTS 5.1 Abbreviations

The abbreviations used throughout the specification to refer to oligonucleotides and/or polynucleotides comprising specific nucleobase sequences are the conventional oneletter abbreviations. Thus, when included in an oligonucleotide or a polynucleotide, the naturally occurring encoding nucleobases are abbreviated as follows: adenine (A), guanine (G), cytosine (C), thymine (T) and uracil (U). Also, unless specified otherwise, polynucleotide sequences that are represented as a series of one-letter abbreviations are presented in the 5'->3' direction.

5.2 Definitions

As used herein, the following terms shall have the following meanings:

"Polynucleotide" and "oligonucleotide" are used interchangeably to refer to a polymer of natural (e.g. A, G, C, T, U) or synthetic nucleobases, or a combination of both. The backbone of the polynucleotide can be composed entirely of "native" phosphodiester linkages, or it may contain one or more modified linkages, such as one or more phosphorothioate, phosphorodithioate, phosphoramidate or other modified linkages. As a specific example, a polynucleotide may be a peptide nucleic acid (PNA), which contains amide interlinkages. Additional examples of synthetic bases and backbones that can be used in conjunction with the invention, as well as methods for their synthesis can be found, for example, in U.S. Pat. No. 6,001,983; Uhlman & Peyman, 1990, Chemical Review 90(4):544–584; Goodchild, 1990, Bioconjugate Chem. 1(3):165–186; Egholm et al., 1992, J. Am. Chem. Soc. 114:1895–1897; Gryaznov et al., J. Am. Chem. Soc. 116:3143–3144, as well as the references cited in all of the above. Common synthetic nucleobases of which polynucleotides may be composed include 3-methlyuracil, 5,6-dihydrouracil, 4-thiouracil, 5-bromouracil, 5-thorouracil, 5-iodouracil, 6-dimethyl aminopurine, 6-methyl aminopurine, 2-aminopurine, 2,6-diamino purine, 6-amino-8-bromopurine, inosine, 5-methylcytosine, 7-deazaadenine, and 7-deazaguanosine. Additional non-limiting examples of synthetic nucleobases of which the target nucleic acid may be composed can be found in Fasman, CRC PRACTICAL HANDBOOK OF BIOCHEMISTRY AND MOLECULAR BIOLOGY, 1985, pp. 385–392; Beilstein's Handbuch der Organischen Chemie, Springer Verlag, Berlin and Chemical Abstracts, all of which provide references to publications describing the structures, properties and preparation of such nucleobases.

"Capturable primer" refers to a molecule comprising a priming moiety and prey moiety.

"Priming moiety" refers to an oligonucleotide that can be used to generate a primer extension product from a template polynucleotide according to techniques known to those of skill in the art. Generally, a priming moiety hybridizes to a template polynucleotide and a primer extension product is generated enzymatically from the priming moiety. The priming moiety is incorporated into the primer extension product. For example, a priming moiety can be used to generate a polynucleotide sequencing ladder or a polynucleotide amplification product.

"Family of primer extension products" refers to one or more polynucleotides generated from the same capturable primer or from different capturable primers that can be selectively immobilized by the same capture compound. For example, a family of primer extension products can be a ladder of primer extension products generated from a capturable sequencing primer. The polynucleotides of a family of primer extension products can be substantially identical, or they can be different. For instance, a family of primer extension products generated in a sequencing reaction can have a plurality of lengths.

"Specific binding pair" refers to a pair of molecules that specifically bind to one another. Examples of specific binding pairs include, but are not limited to polynucleotides with complementary base pairs, antibody-antigen pairs, biotin-avidin pairs, ligand-receptor pairs and other pairs of molecules known to those of skill in the art to specifically bind to one another. Examples of binding pairs include pairs of complementary polynucleotides.

"Prey moiety" refers to a compound or a portion of a compound that, together with a capture compound, forms a specific binding pair of molecules. Examples of prey moieties include polynucleotides that are capable of hybridizing with polynucleotide capture compounds. In one embodiment the prey moiety can be a polynucleotide comprising synthetic bases, such as those described in U.S. Pat. No. 6,001,983, that are capable of hybridizing to synthetic bases of a corresponding capture compound but are not capable of hybridizing to naturally occurring bases. Typically, a polynucleotide prey moiety is a polynucleotide of 5 to 35 nucleotide or a polynucleotide of 15 to 20 nucleotides.

"Capture compound" refers to a compound or a portion of a compound that, together with a prey moiety, forms a specific binding pair. A capture compound can selectively bind a capturable primer and thus can also selectively bind a primer extension product generated from the capturable primer. Examples of capture compounds include polynucleotides that are capable of hybridizing with polynucleotide prey moieties. Thus, a polynucleotide capture compound can be a polynucleotide that is wholly or partially complementary to a prey moiety. In some embodiments, a polynucleotide capture compound is wholly complementary to the prey moiety. A polynucleotide capture compound is typically of 5 to 35 nucleotides or of 15 to 20 nucleotides. In some embodiments, a polynucleotide capture compound is of the same length as a corresponding prey moiety. The capture compound can comprise synthetic bases, such as those described in U.S. Pat. No. 6,001,983, that are capable of hybridizing to synthetic bases of a corresponding prey moiety but not capable of hybridizing to naturally occurring bases.

"Specific elution compound" refers to a compound or a portion of a compound that can be used to selectively disrupt the binding of a specific binding pair of a prey moiety and a capture compound. The specific elution compound can, for instance, selectively bind the capture compound, or it can selectively bind the prey moiety. Examples of specific elution compounds include polynucleotides that are capable of hybridizing with polynucleotide capture compounds or with polynucleotides prey moieties. If a corresponding polynucleotide capture compound comprises synthetic bases, such as those described in U.S. Pat. No. 6,001,983, that are only capable of hybridizing to other synthetic bases, then the specific elution compound can also comprise such synthetic bases at appropriate positions so that the specific elution compound is capable of hybridizing to the capture compound.

"Selective elution" refers to the selective disruption of the interaction between a family of primer extension products and a capture substrate such that the family of primer extension products can be isolated from the capture substrate. Typically, a family of primer extension products can be isolated substantially free of other captured families of primer extension products.

"Melting temperature" or "$T_m$" refers to a quantitative expression of the stability of a hybrid of oligonucleotides. $T_m$ can be calculated according to methods known to those of skill in the art. $T_m$ is typically the temperature at which 50% of a given oligonucleotide is hybridized to a corresponding oligonucleotide under given conditions.

"Capture substrate" refers to a solid support having immobilized thereon one or more capture compounds. A capture substrate can be used to capture one or more families of primer extension products from a mixture.

5.3 Method of Generating and Isolating Families of Primer Extension Products

Figure 6:
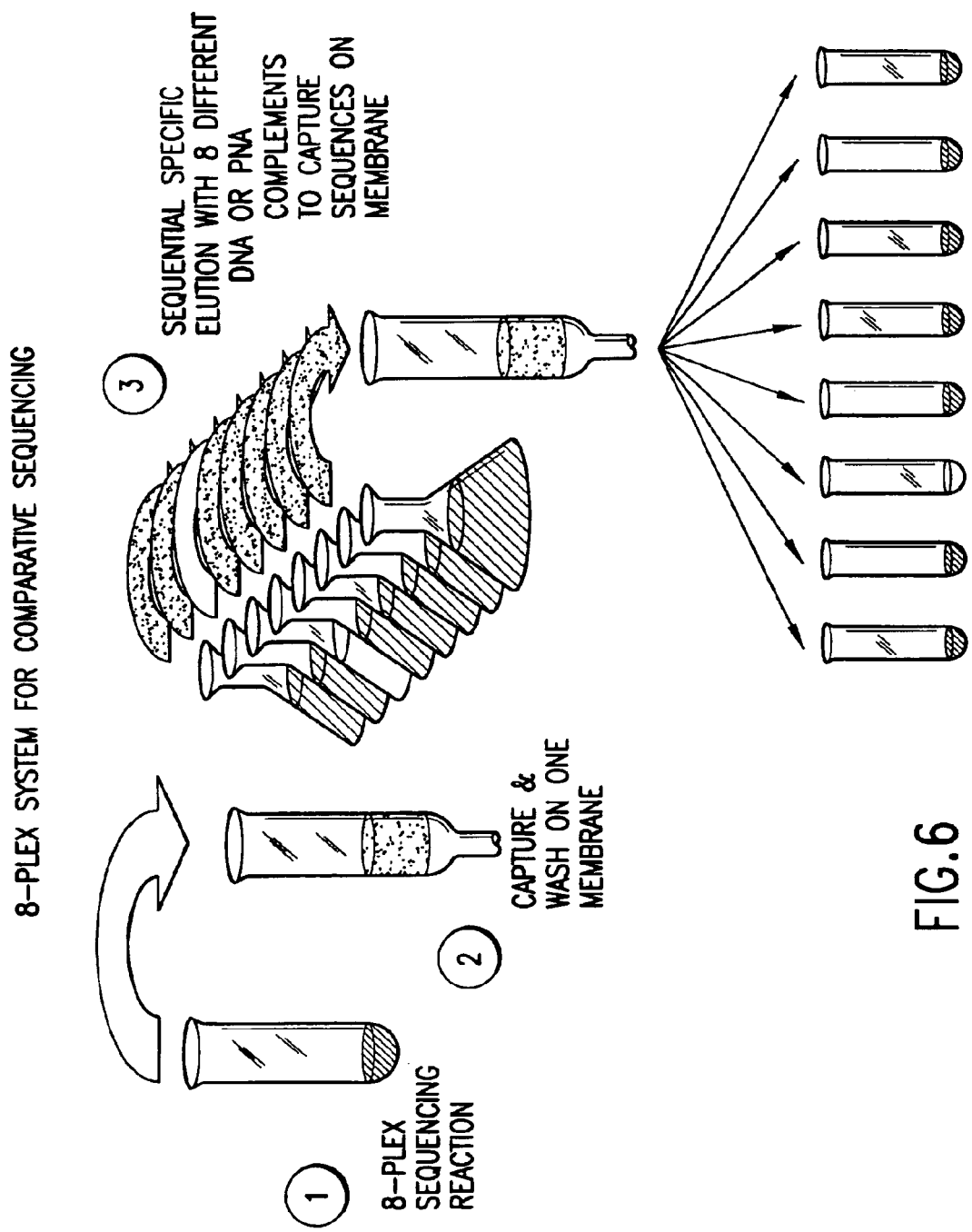
FIG. 6 illustrates an 8-plex sequencing reaction that can be carried out according to the methods of the present invention.
Figure 7:
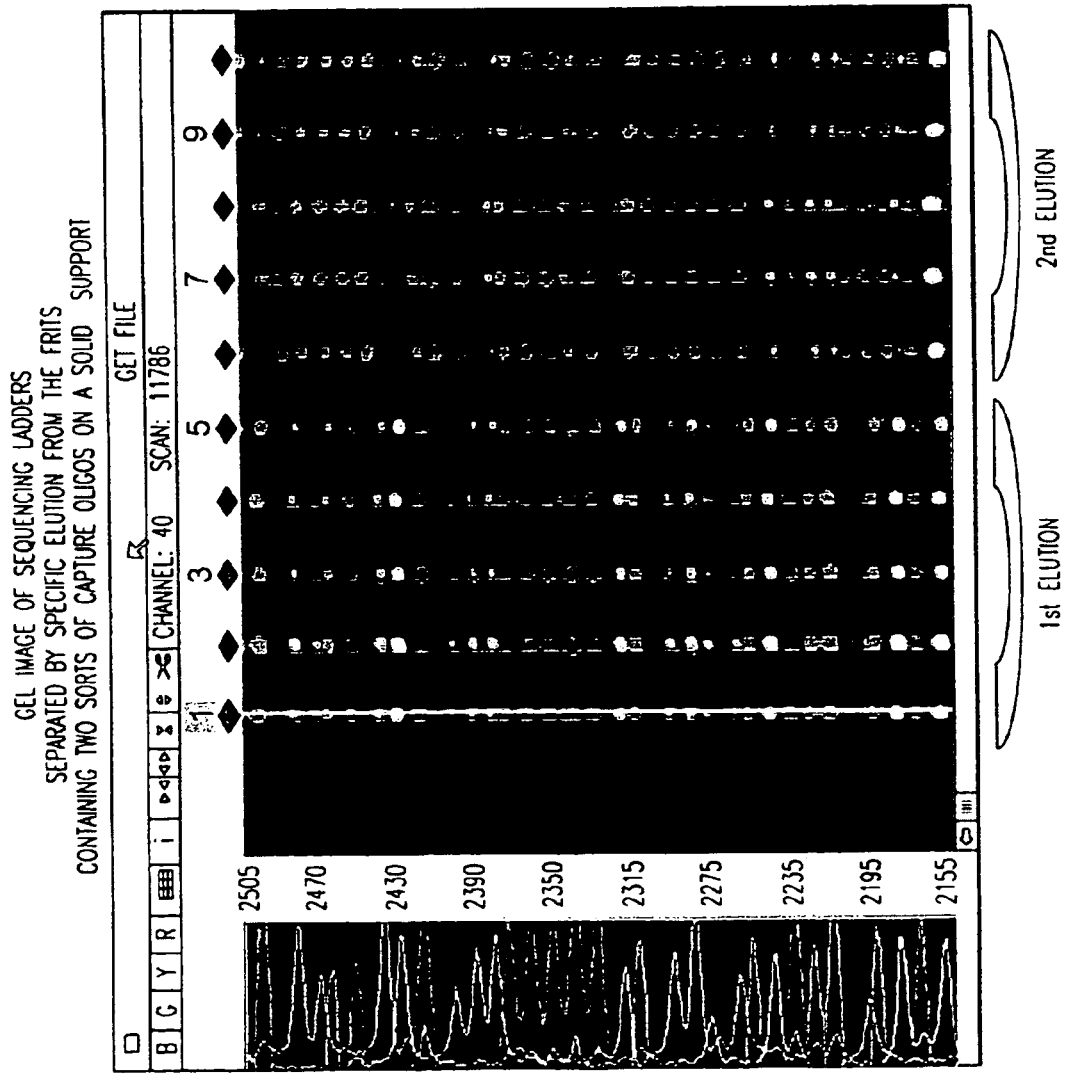
FIG. 7 is a gel image of sequencing ladders of primer extension products separated by specific elution.
Figure 8:
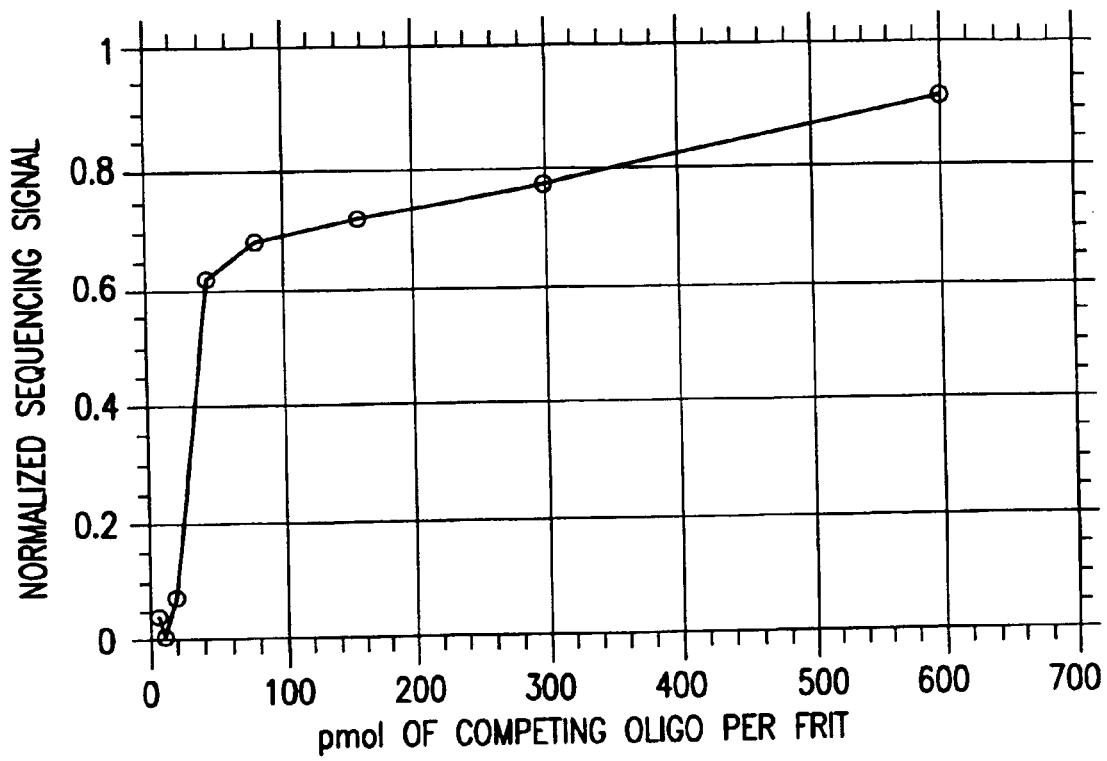
FIG. 8 is a graph summarizing the sequencing signal obtained from sequencing ladders of primer extension products eluted from a capture substrate as a function of concentration of specific elution compound.

According to an embodiment of the present invention, individual captured families of primer extension products can be eluted selectively from a capture substrate. In fact, when a plurality of families of primer extension products are captured on a substrate, each captured family of primer extension products can be eluted sequentially by the selective elution protocol of the present invention. Significantly, a first captured family of primer extension products can be eluted from the capture substrate substantially free of a second captured family of primer extension products and other polynucleotides. A second captured family can then be eluted from the capture substrate substantially free of the first family and other polynucleotides. In the embodiment illustrated in FIG. 6, eight or more multiplexed captured families of primer extension products can be eluted and isolated in this manner.

As illustrated in FIG. 4, capture substrate 28 is a solid support that is capable of having polynucleotides immobilized thereon. Capture substrates are discussed in detail below. Captured polynucleotide 15 and captured polynucleotide 18 are immobilized on capture substrate 28. In the embodiment of the invention illustrated in FIGS. 4 and 5, captured polynucleotide 15 and captured polynucleotide 18 are from different families of polynucleotides. However, capture substrate 28 can have multiple polynucleotides from the same or from different families immobilized thereon. Families of polynucleotides can be prepared according to standard techniques that are discussed below. Capture substrates and methods for capturing polynucleotides on capture substrates are also discussed below.

To selectively elute a first captured family of polynucleotides from capture substrate 28 as illustrated in FIG. 5, a captured family of polynucleotides 15 is contacted with a first specific elution compound 32. Specific elution compounds, which are discussed in detail below, are compounds that are capable of selectively disrupting the binding interaction between a capture compound and a prey moiety. A specific elution compound is capable of selectively disrupting binding if it is capable of disrupting the binding between a first paired capture compound and prey moiety without disrupting the binding between distinct pairs of capture compounds and prey moieties present on the same substrate. In general, specific elution compound 32 competes with prey moiety 12 for the binding of capture compound 20. Upon binding of capture compound 20 with specific elution compound 32, primer extension product 15 comprising prey moiety 12 is released into solution. A released, substantially pure primer extension product 15 can then be recovered from the elution solution for further analysis.

The molar ratio of the specific elution compound 32 to the specific binding pair of capture compound 20 and prey moiety 12 is not critical for success, and can be between 1:1 and 20:1. Generally, the elution efficiency increases with increasing molar ratio. With a 1:1 molar ratio the elution efficiency can be about 50%, depending upon the specific experimental conditions. The efficiency of recovery of a family of primer extension products can be as high as 95% or higher under ideal conditions with the appropriate molar ratio.

Significantly, a second captured family of polynucleotides 18 can then be contacted with a second specific elution compound 34 to selectively elute the second family of primer extension products. Prior to contact with second specific elution compound 34, second captured family of polynucleotides 18 can be optionally washed in order to remove traces of the first family of primer extension products, first specific elution compound 32 and other molecules. Contact with second specific elution compound 34 can proceed as described above for first specific elution compound 32. Second specific elution compound 34 selectively disrupts the binding interaction between a second capture compound 26 and a second prey moiety 16 thereby liberating a second primer extension product 18. A released, substantially purified second family of primer extension products can then be recovered from the elution solution for further analysis.

Furthermore, each captured family of primer extension products can be eluted from the capture substrate in like manner. In fact any number of multiplexed captured families of primer extension products can be isolated from the same capture substrate, each in substantially pure form and each substantially free from contamination by the other families of primer extension products. In one embodiment of the invention, multiplexed captured families of primer extension products are sequentially eluted from capture substrate 28 in the order of their melting temperatures. The captured family of primer extension products immobilized through a specific binding pair with lowest melting temperature is eluted first. The captured family of primer extension products immobilized through a specific binding pair with next lowest melting temperature is eluted second, and so forth. The melting temperature of the captured families can be adjusted according to the melting temperature of the captured family to be eluted, as will be apparent to those of skill in the art.

5.3.1 Specific Elution Compounds

Specific elution compound 34 is a compound that selectively disrupts the binding interaction between capture compound 20 and corresponding prey moiety 12 and/or a captured primer extension product comprising prey moiety 12. In general, a specific elution compound 34 competitively inhibits the binding between a capture compound 20 and a prey moiety 12. Specific elution compound 34 is capable of selective disruption if it can disrupt the binding interaction between captured primer extension product comprising prey moiety 12 and capture compound 20 so that captured primer extension product comprising prey moiety 12 can be isolated substantially free of other captured primer extension products. In certain embodiments, Specific elution compound 34 can be used to isolate a captured primer extension product substantially free of other captured primer extension products captured on the same capture substrate.

A specific elution compound 34 can be any compound known to those of skill in the art to competitively inhibit the binding between a specific binding pair of a capture compound 20 and a prey moiety 12. For instance, if the specific binding pair is a ligand-receptor pair, appropriate specific elution compounds can include, for instance, inhibitors of the binding interaction between the ligand and the receptor, an excess amount of the receptor or an excess amount of the ligand. If the specific binding pair is an antigen-antibody complex, appropriate specific elution compounds can include an excess of the antigen, an excess of an inhibitor of the antibody-antigen binding or an excess of the antibody. Other specific elution compounds will be apparent to those of skill in the art depending on the particular capture compound-prey moiety pair.

In certain embodiments of the invention, the capture compound, the prey moiety and the specific elution compound are all polynucleotides. The capture compound and the prey moiety are wholly or partially complementary polynucleotides that are capable of hybridizing to form a complex. The specific elution compound is a polynucleotide that is capable of selectively disrupting this complex. The polynucleotide specific elution compound can be wholly or partially complementary to the capture compound so that the specific elution compound is capable of selectively disrupting the capture compound-prey moiety complex. Furthermore, in order to increase binding affinity between a specific elution compound and a capture compound, a specific elution compound can be complementary to a portion of the capture compound that does not complement the prey moiety. Such portions include polynucleotide linkers, as discussed below.

In other embodiments, a polynucleotide specific elution compound can be wholly or partially complementary to a polynucleotide prey moiety so long as the polynucleotide specific elution compound is capable of specifically disrupting a complex between the prey moiety and a corresponding capture compound. Furthermore, in order to increase binding affinity between a specific elution compound and primer extension product comprising a prey moiety, the specific elution compound can also be complementary to portions of the primer extension product that do not complement a capture compound. For instance, a specific elution compound can also be wholly or partially complementary to the priming moiety portion of the capturable primer. Depending on the intended use of the family of primer extension products, a specific elution compound can be separated from an isolated primer extension product by any technique known to those of skill in the art.

Polynucleotide specific elution compounds can be chosen so that they have a higher melting temperature in a complex with the capture compound or the prey moiety than the melting temperature of the corresponding capture compound-prey moiety pair. The higher melting temperature can be used to facilitate the competitive disruption of the capture compound-prey moiety pair by adjusting or selecting the stringency of the elution conditions. In addition, a polynucleotide specific elution compound can have greater or more extensive sequence complementarity to capture compound 20 or to prey moiety 12, especially in embodiments where capture compound 20 and prey moiety 12 are partially complementary. In certain embodiments of the invention, specific elution compound 34 displays both a higher melting temperature and greater or more extensive sequence complementarity with the corresponding capture compound 20 or prey moiety 12.

5.3.2 Families of Primer Extension Products

The families of primer extension products can be prepared by any method known to those of skill in the art for preparing polynucleotides. For instance, a family of primer extension products can be generated with a capturable primer. As shown in FIG. 1, capturable primer 10 comprises priming moiety 14 and prey moiety 12, both discussed in detail below. In general, priming moiety 14 is an oligonucleotide capable of initiating a polynucleotide extension reaction, and prey moiety 12 is a moiety capable of binding capture compound 20, illustrated in FIG. 3 and described in detail below. Capturable primers are discussed extensively in PCT publication WO 98/14610, which is hereby incorporated by reference in its entirety.

As shown in FIG. 2, primer extension product 15 can be generated from capturable primer 10 by any polynucleotide extension reaction known to one of skill in the art. For instance, primer extension product 15 can be generated by a sequencing reaction or by a polynucleotide amplification reaction or by any other primer extension reaction known to one of skill in the art. The present method also includes other polynucleotide extension reactions known to those of skill in the art such as the ligation assays described in U.S. Pat. Nos. 4,883,750, 4988,617 and 5,242,794, which are hereby incorporated by reference in their entireties.

Suitable methods of performing polynucleotide extension reactions include those described, for example, in Sambrook et al., 2001, Molecular Cloning, A Laboratory Manual, Third Edition, Cold Spring Harbor Press, N.Y., and in Ausubel et al., 1989, Current Protocols in Molecular Biology, Green Publishing Associates and Wiley Interscience, N.Y., each of which is incorporated herein by reference in its entirety. Suitable polynucleotide extension reactions include primer extension reactions, the polymerase chain reaction, ligase chain reactions, nucleic acid sequence-based amplification and other polynucleotide extension reactions known to one of skill in the art.

In general, capturable primer 10 is contacted with a template oligonucleotide under conditions in which capturable primer 10 is capable of hybridizing with the template polynucleotide. The template polynucleotide can be DNA, RNA or any natural or synthetic polynucleotide capable of serving as a template in a polynucleotide extension reaction. Any further reagents necessary for the primer extension reaction are contacted with capturable primer 10 and the template polynucleotide. Such reagents can include nucleotides and enzymes such as nucleic acid polymerases and other reagents required for the particular primer extension reaction. For instance, in a sequencing reaction chain terminators can also be added to the polynucleotide extension reaction. Completion of the reaction results in primer extension product 15 as shown in FIG. 2. Significantly, primer extension product 15 comprises prey moiety 12 that can be used for the capture of primer extension product 12, as discussed in detail below.

Significantly, because the method of the present invention allows facile isolation of primer extension products from the reaction, a plurality of polynucleotide extension reactions can be carried out simultaneously with a plurality of capturable primers and/or a plurality of template polynucleotides. Multiplex primer extension reactions are discussed extensively in PCT publication WO 98/14610. The polynucleotide extension reactions can even be carried out in the same reaction vessel. If individual primer extension products are to be isolated, each can be generated from a different capturable primer having a unique prey moiety. If families of primer extension products are to be isolated, each primer extension product of a family can be generated from a capturable primer bearing the same prey moiety as the other primer extension products of the family.

If the polynucleotide extension reaction is a sequencing reaction, for instance, a family of primer extension products could be a ladder of primer extension products of varying lengths generated from the same capturable primer and the same polynucleotide template. Sequencing reactions can advantageously be carried out by the cycle-sequencing method described in Murray, 1989, *Nuc. Acids Res.* 17:8889. Sequencing reactions can be terminated by various chain termination methods including labeled terminator sequencing using fluorescent labels or non-fluorescent labels. Labeled primer sequencing can also be used with fluorescent labels or non-fluorescent labels. In certain convenient embodiments, the labels have four colors that are convenient for sequencing applications. Examples of suitable labels and methods of their use are discussed, for example, in Prober et al., 1987, Science 238: 336–341. Furthermore, other labels can be used with the sequencing reactions including enzymatic labels and radioactive labels.

The primer extension reaction can be multiplexed by a factor of two or more. Typically, multiplexing is by a factor of between two and twenty. However, the invention also includes embodiments wherein multiplexing is by factors of more than twenty. The multiplexed capturable primers can prime extension reactions along the same polynucleotide template or along different polynucleotide templates. The different polynucleotide templates can be in the same reaction vessel or in different reaction vessels.

Significantly, primer extension product generated from capturable primers bearing the same prey moiety can be captured from the reaction mixture and subsequently isolated from other primer extension products as described below.

5.3.2.1 Priming Moiety

Priming moiety 14 of capturable primer 10 can be any polynucleotide known to one of skill in the art to be capable of initiating a polynucleotide extension reaction from an appropriate template polynucleotide.

In general, priming moiety 14 is about 12–36 nucleotides in length. However, priming moiety 14 can be of a greater or lesser length so long as priming moiety 14 is capable of initiating a polynucleotide extension reaction. Priming moiety 14 can be capable of hybridizing to a unique segment of a template polynucleotide and can be capable of initiating a primer extension reaction from a polynucleotide template under the appropriate conditions.

Criteria for the design of sequence specific primers are well known to persons of skill in the art. Detailed descriptions of designing primers that can anneal to specific sequences can be found, for example, in Dieffenbach and Dveksler, 1995, *PCR Primer, A Laboratory Manual*, Cold Spring Harbor, Cold Spring Harbor Press, and Kwok et al., 1990, *Nuc. Acids Res.* 18:999–1005, both of which are hereby incorporated by reference in their entirety. Priming moieties can be wholly or partially complementary to a target sequence of the polynucleotide template, so long as priming moiety 14 is capable of initiating a polynucleotide extension reaction. Priming moiety 14 can be wholly complementary to a unique target sequence of the template polynucleotide.

5.3.2.2 Prey Moiety

Prey moiety 12 is a moiety that, together with capture compound 20, forms a specific binding pair. Prey moieties and capture compounds are discussed in detail in PCT publication WO 98/14610, and capture compounds are discussed in detail above.

As illustrated in FIG. 4, prey moiety 12 can be any moiety known to those of skill in the art to be a member of a specific binding pair such that prey moiety 12 can be reversibly and selectively immobilized by capture compound 20. Specific binding pairs useful in this method include, for example, pairs of oligonucleotides capable of hybridizing with each other, ligand—receptor pairs, biotin—avidin pairs and antibody-antigen pairs. Prey moiety 12 can be either member of these specific binding pairs or other specific binding pairs known to those of skill in the art. Capture compound 20, discussed in detail below, can be the other member of the pair or any other moiety capable of forming a specific binding pair with prey moiety 12. When primer extension product 15 is to be isolated from a mixture of polynucleotides, capture compound 20 can be capable of selectively binding prey moiety 12, and thus should not be capable of forming stable complexes with other molecules in a mixture of primer extension products such as template polynucleotides, priming moieties and other prey moieties.

Although many classes of molecules can be used as prey moieties, in some embodiments, prey moieties are polynucleotides that are capable of specifically binding to a polynucleotide capture compound. In general, a polynucleotide prey moiety is not be capable of significant hybridization to other molecules in a mixture of primer extension products such as a template polynucleotide, recovery primers or other prey moieties. However, a polynucleotide prey moiety may comprise all, none or a portion of a priming moiety, so long as the prey moiety does not interfere with the priming of the primer extension reaction and so long as the priming moiety does not interfere with reversible capture of the capturable primer, as discussed below. In certain embodiments, a polynucleotide prey moiety is not complementary to the template oligonucleotide.

In one embodiment of the invention, prey moiety 12 and capture compound 20, discussed in detail below, comprise synthetic nucleobases that are capable of base pairing only with other synthetic nucleobases and not with naturally occurring nucleobases. Such synthetic nucleobases are disclosed in U.S. Pat. No. 6,001,983 which is hereby incorporated by reference in its entirety. Prey moieties and capture compounds comprising such synthetic nucleobases are capable of hybridizing with each other but not with other polynucleotides of a primer extension reaction mixture. The use of such prey moieties and capture compounds reduces or eliminates the non-selective binding of prey moieties or capture compounds to other molecules in a mixture of primer extension products.

Polynucleotide prey moiety 12 can be isolated from biological samples, generated by PCR reactions or other template-specific reactions, or made synthetically. Methods for isolating polynucleotides from biological samples and/or PCR reactions are well-known in the art, as are methods for synthesizing and purifying synthetic polynucleotides.

Prey moiety 12 can be linked to priming moiety 14 by any means for linking two moieties known to those of skill in the art. For instance, prey moiety 12 can be linked to primer 14 oligonucleotide via direct covalent bond. Alternatively, prey moiety 12 can be linked to priming moiety 14 via a spacer known to those of skill in the art such as a bifunctional linker. When prey moiety 12 is a polynucleotide, a suitable linkage between prey moiety 12 and priming moiety 14 is a direct phosphodiester linkage, or an analog thereof, between the two. Also suitable is a linkage of one or more nucleotides linked by phosphodiester linkages, or analogs thereof. It is important that prey moiety 12 and the linkage between prey moiety 12 and priming moiety 14 not interfere with the priming of the primer extension reaction by priming moiety 14. A suitable capturable primer is a polynucleotide comprising a polynucleotide prey moiety and a priming moiety and an optional polynucleotide linker between the two. When the capturable primer is to be used in a PCR reaction, the polynucleotide prey moiety and the polynucleotide priming moiety can conveniently be linked by a polynucleotide linker, for instance, to facilitate the PCR reaction.

While a polynucleotide prey moiety 12 can be any number of nucleotides in length, it will typically be composed of a number of nucleotides sufficient to permit efficient, specific hybridization at moderate temperatures, while at the same time minimizing the occurrence of secondary structure. Generally, polynucleotide prey moieties will be composed of about 7 to 40 nucleotides, typically about 10 to about 25 nucleotides or about 15 to about 20 nucleotides.

As illustrated in FIG. 4, prey moiety 12 can be used to reversibly and selectively bind primer extension product 15, comprising capturable primer 10, to capture compound 20. The selectivity of the binding interaction between prey moiety 12 and capture compound 20 permits selective capture of a family of primer extension products comprising prey moiety 12 from a complex mixture of primer extension products. For instance, all primer extension products that comprise a sequencing ladder generated from a single capturable primer can be selectively immobilized on corresponding capture compounds.

Other families of primer extension products can be selectively immobilized by reversible binding to other capture compounds such as capture compound 26. Significantly, because individual families of primer extension products can be selectively eluted from capture substrate 28 as discussed in detail below, capture substrate 28 can comprise multiple capture compounds and can thereby be used to immobilize multiple families of primer extension products. If a reaction mixture comprises multiple families of primer extension products to be isolated, the pairs of prey moieties and capture compounds can be capable of forming selective complexes under compatible conditions.

5.3.3 Capture of Primer Extension Products with a Capture Substrate

Capture substrates having families of primer extension products immobilized thereon can be prepared according to any method known to those of skill in the art. For instance, a mixture of families of primer extension products can be reversibly immobilized on capture substrate 28 as shown in FIG. 3. Capture substrate 28 comprises at least one capture compound 20. Significantly, capture substrate 28 can comprise a plurality of capture compounds, such as capture compound 20 and capture compound 26. In some embodiments, a capture substrate comprises multiple capture compounds, each corresponding to a prey moiety of a family of primer extension products to be captured from a mixture of primer extension products. If capture substrate 28 comprises multiple capture compounds, capture substrate 28 can be used advantageously to reversibly immobilize a plurality of families of primer extension products from a mixture of primer extension products in one step. Capture substrates and capture compounds are discussed in detail below.

In use, a sample containing or suspected of containing a family of polynucleotides is contacted with the capture substrate. Prior to application of the sample, the capture substrate may be washed with buffer to equilibrate the capture substrate to the conditions that will be used for capture. If capture substrate 28 is a polynucleotide, capture substrate 28 may also be treated to disrupt any secondary structure in the capture compounds, either by washing with denaturing buffers or by application of heat. The mixture of primer extension products can also be treated to eliminate duplex polynucleotides and to disrupt secondary structures.

The conditions under which a mixture of primer extension products are contacted with a capture substrate depend on the binding properties of pairs of capture compounds and prey moieties and will be apparent to one of skill in the art. For instance, when a prey moiety and a corresponding capture compound are complementary polynucleotides, the contact conditions can be conditions under which the prey moiety and the capture compound selectively hybridize to form a complex. Specific conditions for capture including polynucleotide sequence, polynucleotide concentration, density of capture compounds on the capture substrate, volumes, pH, buffer, salt concentration, incubation time, temperature and so forth are within the knowledge of those of skill in the art. Pairs of prey moieties and capture compounds are chosen so that each pair can form an immobilized complex under similar or identical conditions. Typically, a DNA prey moiety can be contacted with a DNA capture compound in, for example, 100 mM NaCl or 100 mM ammonium acetate. Less salt can be used for pairs comprising RNA and much lower salt concentrations can be used for PNA-PNA, PNA-RNA or PNA-DNA pairs. If the pair is PNA-PNA, very little or no salt can be used in the capture conditions.

As the sample flows through and contacts the capture substrate, selective binding takes place. Thus, the sample typically contacts the capture substrate for a period of time that is long enough for binding to occur. The kinetics of binding will depend on many factors. For instance when prey moiety 12 and capture compound 20 are hybridizing polynucleotides, the factors include the sequences of prey moiety 12 and capture compound 20, the GC content of prey moiety 12 and capture compound 20, the lengths of prey moiety 12 and capture compound 20, the amount of capture compound 20 immobilized on capture substrate 28, the concentration of prey moiety 12 in the sample, the salt and/or buffer conditions of the sample, the temperature of hybridization, etc. Such conditions will be apparent to one of skill in the art.

Capture substrate 28 can be optionally washed to remove non-specifically immobilized polynucleotides and other non-specifically immobilized molecules that remain on capture substrate 28. Methods of washing a substrate with immobilized oligonucleotides are within the knowledge of those of skill in the art. The wash solutions can be assayed for the presence of molecules, for example by UV absorbence, to monitor the progress of the washing. Other methods of detecting polynucleotides and other molecules are well known to those of skill in the art.

As discussed in detail above, individual families of primer extension products can be eluted in substantially pure form from a capture substrate that has captured a mixture of families of primer extension products.

5.3.3.1 Capture Substrate

Capture substrate 28 comprises one or more solid supports to which capture compounds can be immobilized. The only requirement of capture substrate 28 is that capture compounds immobilized thereon be capable of selectively binding primer extension products comprising prey moieties that correspond to the capture compounds. Thus, capture substrate 28 can be a filter or a membrane, such as a nitrocellulose or nylon, glass, polymers such as polyacrylamide, gels such as agarose, dextran, cellulose, polystyrene, latex, or any other material known to those of skill in the art to which capture compounds can be immobilized. Advantageously, capture substrate 28 can be composed of a porous material such as those described in copending U.S. application Ser. No. 09/204,865 which is hereby incorporated by reference in its entirety. Exemplary porous materials include, for example, acrylic, styrene-methyl methacrylate copolymers, ethylene/acrylic acid and other porous materials described in detail in Ser. No. 09/204,865. When capture substrate 28 comprises multiple solid supports, each solid support can have one or more capture compounds or families of primer extension products immobilized thereon.

Capture substrate 28 can take on any form so long as the form does not prevent derivatization with capture compounds and does not prevent reversible capture of prey moieties and primer extension products generated from capturable primers. For instance, capture substrates can have the form of disks, slabs, strips, beads, submicron particles, coated magnetic beads, gel pads, microtiter wells, slides, membranes, frits or other forms known to those of skill in the art. The capture substrate is optionally disposed within a housing, such as a chromatography column, spin column, syringe-barrel, pipette, pipette tip, 96 or 384-well plate, microchannels, capillaries, etc., that aids the flow of liquids through the capture substrate. In certain embodiments of the invention, capture substrate 28 comprises multiple solid supports, such as the porous materials discussed above, disposed in a housing such as a syringe barrel. Each solid support can have one or more capture compounds or families of polynucleotides immobilized thereon. Additionally, materials having suitable average pore sizes and porosities are available commercially, and are either available in suitable thicknesses or can be cut into slabs, strips, disks or other convenient shapes of suitable thickness.

Derivatazation of capture substrate 28 with capture compounds is described in detail below.

5.3.3.2 Capture Compounds

Capture compound 20 forms a specific binding pair with prey moiety 12 of a family of primer extension products. Capture compound 20 can be capable of selectively binding a family of primer extension products bearing prey moiety 12 out of a mixture of polynucleotides. As illustrated in FIG. 4, capture compound 20 can be any moiety known to those of skill in the art to be a member of a specific binding pair such that prey moiety 12 can be reversibly and selectively immobilized by capture compound 20. Specific binding pairs useful in this method include, for example, pairs of oligonucleotides capable of hybridizing with each other, ligand-receptor pairs, biotin-avidin pairs and antibody antigen pairs. Capture compound 20 can be either member of these specific binding pairs or other specific binding pairs known to those of skill in the art so long as capture compound 20 can selectively bind prey moiety 12. When primer extension product 15 is to be isolated from a mixture of polynucleotides, capture compound 20 can be capable of selectively binding prey moiety 12, and thus not be capable of forming stable complexes with other molecules in a mixture of primer extension products such as template polynucleotides, priming moieties and other prey moieties. Typically, capture compound 20 is a polynucleotide capable of selective hybridization with a polynucleotide prey moiety 12.

If capture compound 20 and prey moiety 12 are polynucleotides, then capture compound 20 can be at least partially complementary to prey moiety 12. In certain embodiments, capture compound 20 is 100% complementary to prey moiety 12. A polynucleotide capture compound may be composed entirely of deoxyribonucleotides, entirely of ribonucleotides, or may be composed of mixtures of deoxy- and ribonucleotides. Due to their stability to RNases and high temperatures, as well as their ease of synthesis, capture polynucleotides composed entirely of deoxyribonucleotides are suitable. In certain embodiments, the melting temperature of a prey moiety and a capture compound is between 50° C. and 70° C. so that nonspecific binding in the capture step, discussed below, can be eliminated by washing under low or moderate stringency conditions. In one embodiment of the invention the melting temperature is about 70° C.

A polynucleotide capture compound 20 can be composed of all natural or all synthetic nucleotide bases, or a combination of both. While in most instances the capture polynucleotide will be composed entirely of the natural bases (A, C, G, T or U), in certain circumstances synthetic bases may be used. In one embodiment, a polynucleotide capture compound 20 and polynucleotide prey moiety 12 are composed of synthetic nucleobases that hybridize only to other synthetic nucleobases and not to naturally occurring nucleobases. Such synthetic nucleobases are described, for example, in U.S. Pat. No. 6,001,983. Moreover, while the backbone of polynucleotide capture compound 20 will typically be composed entirely of "native" phosphodiester linkages, it may contain one or more modified linkages, such as one or more phosphorothioate, phosphoramidite or other modified linkages. As a specific example, the polynucleotide recovery capture compound may be a peptide nucleic acid (PNA), which contains amide interlinkages. In some embodiments of the invention, the polynucleotide capture compound can have a minimally charged backbone, a neutral backbone or a positively charged backbone.

While a polynucleotide capture compound will often be a contiguous stretch of nucleotides, it need not be. Stretches of nucleotides can be interrupted by one or more linker molecules that do not participate in sequence-specific base pairing interactions with the target nucleic acid. The linker molecules may be flexible, semi-rigid or rigid, depending on the desired application. A variety of linker molecules useful for spacing one molecule from another or from a solid surface have been described in the art (and are described more thoroughly infra); all of these linker molecules can be used to space regions of capture compound 20 from one another or to space capture compound 20 from capture substrate 28. In some embodiments of this aspect of the invention, a linker moiety is from one to ten, or two to six, alkylene glycol moieties. Examples of linker moieties include ethylene glycol moieties. In one embodiment, the linker is tetraethylene glycol.

While a polynucleotide capture compound 20 can be any number of nucleotides in length, it will typically be composed of a number of nucleotides sufficient to permit minimizing the occurrence of secondary structure. Generally, polynucleotide capture compounds will be composed of about 7 to 40 nucleotides, typically about 10 to about 25 nucleotides or about 15 to about 20 nucleotides. In certain embodiments, polynucleotide capture compounds are of the same length as their corresponding polynucleotide prey moieties.

Polynucleotide capture compound 20 can be isolated from biological samples, generated by PCR reactions or other template-specific reactions, or made synthetically. Methods for isolating polynucleotides from biological samples and/or PCR reactions are well-known in the art, as are methods for synthesizing and purifying synthetic polynucleotides. Polynucleotide capture compounds isolated from biological samples and/or PCR reactions may, depending on the desired mode of immobilization, require modification at the 3'- or 5'-terminus, or at one or more bases, as will be discussed more thoroughly below. Moreover, since the polynucleotide capture compound must be capable of hybridizing to the target nucleic acid, if not already single stranded, it can be rendered single stranded, either before or after immobilization on capture substrate 28.

Capture compound 20 can be immobilized on capture substrate 28 by any technique known to those of skill in the art for immobilizing molecules on solid supports. For example, capture compound 20 can be adsorbed or otherwise non-covalently associated with capture substrate 28; it may be covalently attached to capture substrate 28; or its association may be mediated by specific binding pairs, such as biotin and streptavidin.

In order to effect covalent attachment, capture substrate 28 must first be activated, i.e., treated so as to create reactive groups on or within the substrate that can react with the capture polynucleotide to form a covalent linkage. Those of skill in the art will recognize that the desired reactive group will depend on the chemistry used to attach capture compound 20 to capture substrate 28 and the composition of capture substrate 28. Typical reactive groups useful for effecting covalent attachment of the capture polynucleotide to the porous substrate include hydroxyl, sulfonyl, amino, epoxy and carboxyl groups; however, other reactive groups as will be apparent to those having skill may also be used and are also included within the scope of the invention.

For a review of the myriad techniques that can be used to activate the capture substrates of the invention with a sufficient density of reactive groups, see, the Wiley Encyclopedia of Packaging Technology, 2d Ed., Brody & Marsh, Ed., "Surface Treatment," pp. 867–874, John Wiley & Sons (1997), and the references cited therein (hereinafter "Surface Treatment"). Chemical methods suitable for generating amino groups on silicon oxide substrates are described in Atkinson & Smith, "Solid Phase Synthesis of Oligodeoxyribonucleotides by the Phosphite Triester Method," In: Oligonucleotide Synthesis: A Practical Approach, M J Gait, Ed., 1984, IRL Press, Oxford, particularly at pp. 45–49 (and the references cited therein); chemical methods suitable for generating hydroxyl groups on silicon oxide substrates are described in Pease et al., 1994, Proc. Natl. Acad. Sci. USA 91:5022–5026 (and the references cited therein); chemical methods for generating functional groups on polymers such as polystyrene, polyamides and grafted polystyrenes are described in Lloyd-Williams et al., 1997, Chemical Approaches to the Synthesis of Peptides and Proteins, Chapter 2, CRC Press, Boca Raton, Fla. (and the references cited therein).

Linkers suitable for spacing biological molecules such as capture compounds from solid surfaces are well-known in the art, and include, by way of example and not limitation, polypeptides such as polyproline or polyalanine, saturated or unsaturated bifunctional hydrocarbons such as 1-aminohexanoic acid, polymers such as polyethylene glycol, etc. In certain embodiments, the linker is polyethylene glycol (MW 100 to 1000). 1,4-Dim ethoxytrityl-polyethylene glycol phosphoramidites useful for forming phosphodiester linkages with hydroxyl groups, as well as methods for their use in nucleic acid synthesis on solid substrates, are described, for example in Zhang et al., 1991, Nucl. Acids Res. 19:3929–3933 and Durand et al., 1990, Nucl. Acids Res. 18:6353–6359. Other methods of attaching polyethylene glycol linkers will be apparent to those of skill in the art.

In addition, the capture compound may comprise polynucleotide linkers that may or may not hybridize to the prey moiety. In some embodiments, these polynucleotide linkers are not capable of hybridizing to the prey moiety or to any portion of a primer extension product of a multiplexed reaction mixture. However, these polynucleotide linkers can be complementary to a portion of a specific elution compound, as discussed in detail above.

5.4 Kits for Generating and Isolating Multiplex Primer Extension Products

Generally, the kits comprise a capture substrate of the invention having immobilized thereon a capture compound capable of selectively binding with a corresponding prey moiety. The kits farther comprise a prey moiety corresponding to the capture compound and/or a recovery primer comprising the prey moiety. The kit may additionally comprise one or more other reagents or components useful for performing a particular assay. Alternatively, the kits can comprise a three dimensional substrate activated with a reactive functional group and a capture compound modified with a group capable of forming a covalent linkage with the activated substrate, or means for synthesizing a capture compound on the activated substrate, such as nucleoside phosphoramidites and/or other DNA or RNA synthesis reactants or reagents. Optional components that can be included with the kits include housings in which the substrates can be disposed, sequencing templates and dideoxynucleotide reagents and enzymes for generating sequencing ladders from the target nucleic acid, polymerases and primers for amplifying the target nucleic acid, linkers for spacing the target nucleic acid from the porous substrate and buffers and reagents useful for sequencing, amplification and/or other nucleic acid applications.

Various embodiments of the invention have been described. The descriptions and examples are intended to be illustrative of the invention and not limiting. Indeed, it will be apparent to those of skill in the art that modifications may be made to the various embodiments of the invention described without departing from the spirit of the invention or scope of the appended claims set forth below.

All references cited herein are hereby incorporated by reference in their entirety.

What is claimed is:

1. A method of isolating a plurality of families of primer extension products from a capture substrate comprising the steps of:

(a) contacting a plurality of captured families of primer extension products with a first specific elution compound thereby selectively eluting a first family of primer extension products captured on the capture substrate, wherein the first specific elution compound is a polynucleotide; and (b) contacting the remainder of the plurality of captured families of primer extension products with a second specific elution compound thereby selectively eluting a second family of primer extension products captured on the capture substrate.

2. The method of claim 1 wherein the second specific elution compound is a polynucleotide.

3. The method of claim 2 wherein the families of primer extension products are polynucleotide sequencing ladders.

4. The method of claim 2 wherein the families of primer extension products are polynucleotide amplification products.

5. The method of claim 2 wherein the capture substrate is a continuous solid support.

6. The method of claim 2 wherein the capture substrate comprises a plurality of solid supports.

7. The method of claim 6 wherein the capture substrate comprises a plurality of beads.

8. The method of claim 6 wherein each solid support comprises a plurality of different capture compounds.

9. A method of isolating a plurality of families of primer extension products comprising the steps of:

(a) contacting a plurality of families of primer extension products with a capture substrate, wherein
  (i) a first family of primer extension products comprises a first prey moiety,
  (ii) a second family of primer extension products comprises a second prey moiety, and
  (iii) said capture substrate comprises a first capture compound that is capable of specifically binding the first prey moiety, and a second capture compound that is capable of specifically binding the second prey moiety, under conditions wherein the first family of primer extension products is capable of selectively binding the first capture compound and the second family of primer extension products is capable of selectively binding the second capture compound, (b) selectively eluting a first family of primer extension products and a second family of primer extension products from the capture substrate according to claim 2.

10. The method of claim 9 wherein the first and second prey moieties are polynucleotide.

11. The method of claim 9 wherein the first and second capture compounds are polynucleotide.

12. A method for isolating a plurality of families of primer extension products comprising the steps of:

(a) generating a plurality of families of primer extension products from a plurality of capturable primers and a polynucleotide template, and (b) isolating the plurality of families of primer extension products according to claim 9.

13. A method for isolating a plurality of families of primer extension products comprising the steps of:

(a) generating a plurality of families of primer extension products from a plurality of capturable primers and a plurality of polynucleotide templates, and (b) separating the plurality of families of primer extension products according to claim 9.

* * * * *

UNITED STATES PATENT AND TRADEMARK OFFICE
CERTIFICATE OF CORRECTION

PATENT NO.         : 6,942,974 B2
APPLICATION NO. : 10/096176
DATED               : September 13, 2005
INVENTOR(S)       : Maxim G. Brevnov It is certified that error appears in the above-identified patent and that said Letters Patent is hereby corrected as shown below:

Please insert the following paragraph beginning on column 1, line 5, after the Title of the Invention:

This work was supported at least in part from the U.S. government under National Institute of Standards and Technology Grant No. 70NANB4002. The U.S. government may have certain rights in the inventions recited herein.

Signed and Sealed this

Twenty-eighth Day of November, 2006

JON W. DUDAS
*Director of the United States Patent and Trademark Office*